(12) United States Patent
Bouvier et al.

(10) Patent No.: US 8,128,943 B2
(45) Date of Patent: Mar. 6, 2012

(54) USE OF OXAZOLE DERIVATIVES FOR CONTROLLING FISH PARASITES

(75) Inventors: Jacques Bouvier, Neuchâtel (CH); John Marshall, Royston (GB); Richard Hunter, Royston (GB)

(73) Assignee: Novartis AG, Basel (CH)

( * ) Notice: Subject to any disclaimer, the term of this patent is extended or adjusted under 35 U.S.C. 154(b) by 372 days.

(21) Appl. No.: 11/991,287

(22) PCT Filed: Aug. 28, 2006

(86) PCT No.: PCT/EP2006/008399
§ 371 (c)(1),
(2), (4) Date: Aug. 4, 2010

(87) PCT Pub. No.: WO2007/025694
PCT Pub. Date: Mar. 8, 2007

(65) Prior Publication Data
US 2010/0303865 A1    Dec. 2, 2010

(30) Foreign Application Priority Data
Aug. 29, 2005   (EP) ..................................... 05018677

(51) Int. Cl.
A61K 39/00   (2006.01)
A61K 31/42   (2006.01)
(52) U.S. Cl. ..................................... 424/265.1; 514/374
(58) Field of Classification Search .................. None
See application file for complete search history.

(56) References Cited

U.S. PATENT DOCUMENTS

| | | | |
|---|---|---|---|
| 5,705,516 A | 1/1998 | Turnbull et al. | |
| 6,172,093 B1 | 1/2001 | Lantzsch et al. | |
| 6,413,912 B2 * | 7/2002 | Hall | 504/266 |
| 2001/0011065 A1 | 8/2001 | Hall | |
| 2002/0137781 A1 | 9/2002 | Froelich et al. | |
| 2003/0191169 A1 * | 10/2003 | Sandino et al. | 514/378 |

FOREIGN PATENT DOCUMENTS

| | | |
|---|---|---|
| CA | 2223147 A1 | 12/1996 |
| DE | 19727889 A1 | 1/1999 |
| EP | 0686345 A1 | 12/1995 |

OTHER PUBLICATIONS

International Search Report (noted on the IDS as "ISR") for PCT/EP2006/008399; completed Nov. 13, 2006, filed in the present Application on Jun. 1, 2010.*

International Preliminary Examination Report (noted on the IDS as "Written Opinion") for PCT/EP2006/008399; completed Mar. 4, 2008, filed in the present Application on Jun. 1, 2010.*

* cited by examiner

*Primary Examiner* — Robert A Wax
*Assistant Examiner* — Jeffrey T Palenik

(57) ABSTRACT

The present invention relates to the use of compounds of formula (I), wherein $R_1$, X, Y, Z and m are as defined in the description, in the free form or in salt form either alone or in combination with a vaccine component, for controlling fish parasites, in particular sea lice.

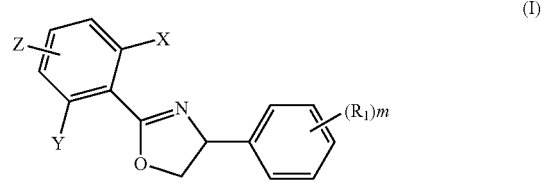

19 Claims, No Drawings

USE OF OXAZOLE DERIVATIVES FOR CONTROLLING FISH PARASITES

This application is a U.S. National Stage application of International Application No. PCT/EP2006/008399 filed Aug. 28, 2006, which claims the benefit of European Application No. EP 05018677.4, filed Aug. 29, 2005, the entire contents of both are hereby incorporated herein by reference.

The present invention relates to the use of the compounds of formula

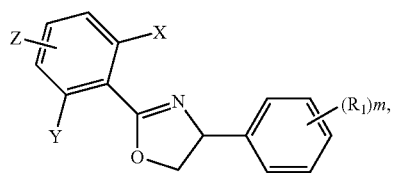

wherein
X and Y, independently of each other, are hydrogen, $C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, cyano-$C_1$-$C_4$-alkyl, cyano-$C_1$-$C_4$-haloalkyl, cyano-$C_1$-$C_4$-alkoxy, cyano-$C_1$-$C_4$-haloalkoxy, cyano-$C_1$-$C_4$-alkylthio, cyano-$C_1$-$C_4$-haloalkylthio, halogen, amino, cyano or nitro;
Z is hydrogen, halogen, $C_1$-$C_4$-alkyl, $C_1$-$C_4$-alkoxy or di($C_1$-$C_4$-alkyl)amino;
$R_1$ is $C_1$-$C_4$-alkyl, $C_1$-$C_4$-haloalkyl, $C_1$-$C_4$-alkoxy, $C_1$-$C_4$-haloalkoxy, $C_1$-$C_4$-haloalkylthio, halogen or unsubstituted or one- or twofold substituted phenyl, the substituents being selected from the group consisting of $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, cyano-$C_1$-$C_4$-alkyl, cyano-$C_1$-$C_4$-haloalkyl, cyano-$C_1$-$C_4$-alkoxy, cyano-$C_1$-$C_4$-haloalkoxy, cyano-$C_1$-$C_4$-alkylthio, cyano-$C_1$-$C_4$-haloalkylthio, $C_2$-$C_6$-alkenyl, $C_2$-$C_6$-haloalkenyl, $C_2$-$C_6$-alkenyloxy, $C_2$-$C_6$-haloalkenyloxy, $C_2$-$C_6$-alkinyl, $C_2$-$C_6$-haloalkinyl, $C_2$-$C_6$-alkinyloxy, $C_2$-$C_6$-haloalkinyloxy, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, OC(O)$R_2$ and halogen, whereby when m or the number of substituents on phenyl independently from each other are more than 1, the substituents may be the same or different;
$R_2$ is $C_1$-$C_4$-alkyl, $C_1$-$C_4$-alkoxy, $C_2$-$C_6$-alkenyl, $C_2$-$C_6$-alkenyloxy, $C_2$-$C_6$-alkinyl, $C_2$-$C_6$-alkinyloxy, $C_3$-$C_8$-cycloalkyl, $C_3$-$C_8$-cycloalkyloxy, $C_3$-$C_8$-halocycloalkyl-$C_1$-$C_4$-alkyl, $C_3$-$C_8$-halocycloalkyl-$C_1$-$C_4$-alkyloxy, N($R_3$$R_4$) or unsubstituted or mono- to penta-substituted phenyl, whereby the substituents are selected from the group comprising $C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, halogen, cyano and nitro;
$R_3$ is hydrogen or $C_1$-$C_4$-alkyl;
$R_4$ is $C_1$-$C_4$-alkyl, $C_1$-$C_4$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, unsubstituted or mono to penta-substituted phenyl or unsubstituted or mono- to penta-substituted phenyl-$C_1$-$C_4$-alkyl, whereby independently of each other, the substituents are respectively selected from the group comprising $C_1$-$C_4$-alkyl; and
m is 0, 1 or 2;
and their enantiomers, in each case either in free form or in the form of a salt; for controlling fish parasites, in particular sea lice. The compound of the formula I is used either alone or in combination with a vaccine component. The invention also relates to a method of controlling these parasites as well as to the use of these compounds or enantiomers for the preparation of corresponding antiparasitic compositions.

The compounds of formula I are known from literature, for example from EP 0,432,661, EP 0,696,584, DE 19,523,388 and U.S. Pat. No. 6,413,912, primarily for pest control in the field of crop protection.

The compounds of formula I are present in the form of enantiomers. The preparation and isolation of enantiomers is described in WO 00/58291. Accordingly, any reference to compounds of formula I hereinbefore and hereinafter is understood to include also their pure enantiomeric forms, even if the latter are not specifically mentioned in each case.

The compounds of formula I can form salts, for example acid addition salts. These are formed for example with strong inorganic acids, typically mineral acids, e.g. sulfuric acid, a phosphoric acid or a halogen acid, or with strong organic carbonic acids, typically $C_1$-$C_4$-alkanecarbonic acids substituted where appropriate for example by halogen, e.g. acetic acid, such as dicarbonic acids that are unsaturated where necessary, e.g. oxalic, malonic, maleic, fumaric or phthalic acid, typically hydroxycarbonic acids, e.g. ascorbic, lactic, malic, tartaric or citric acid, or benzoic acid, or with organic sulfonic acids, typically $C_1$-$C_4$alkane or arylsulfonic acids substituted where appropriate for example by halogen, e.g. methane-sulfonic or p-toluenesulfonic acid. In a broader sense, compounds of formula I with at least one acid group can form salts with bases. Suitable salts with bases are for example metal salts, typically alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl, diethyl, triethyl or dimethylpropylamine, or a mono-, di- or trihydroxy-lower alkylamine, e.g. mono-, di- or triethanolamine. Furthermore, where appropriate corresponding internal salts may also be formed. The free form is preferred. Among the salts of compounds of formula I, the hydrochemically beneficial salts are preferred. Hereinbefore and hereinafter, the free compounds of formula I and their salts are understood where appropriate to include also by analogy the corresponding salts or free compounds of formula I. The same applies for the pure enantiomers of formula I and salts thereof.

Unless otherwise defined, the general terms used hereinabove and hereinbelow have the meanings given hereinbelow.

The halogen atoms considered as substituents of halogenalkyl and halogen-alkoxy are fluorine, chlorine, bromine and iodine, with fluorine and chlorine being preferred.

If not defined to the contrary, carbon-containing groups and compounds contain preferably 1 to 4 inclusive, especially 1 or 2, carbon atoms.

Alkyl—as a group per se and as structural element of other groups and compounds such as alkoxy, halogen-alkyl or halogen-alkoxy—is, in each case with due consideration of the specific number of carbon atoms in the group or compound in question, either straight-chained or branched, and is methyl, ethyl, propyl, isopropyl, butyl, isobutyl, sec.-butyl or tert.-butyl or one of the respective isomers thereof. Preferred alkyl groups are $C_1$-$C_2$-alkyl groups, especially methyl groups.

Cycloalkyl—as a group per se and as structural element of other groups and compounds such as halocycloalkyl, cycloalkoxy and cycloalkylthio,—is, in each case with due consideration of the specific number of carbon atoms in the group or compound in question, cyclopropyl, cyclobutyl, cyclopentyl, cyclohexyl, cycloheptyl or cyclooctyl.

Alkenyl—as a group per se and as structural element of other groups and compounds, such as alkenyloxy—is, in each case with due consideration of the specific number of carbon atoms in the group or compound in question and of the conjugated or isolated double bonds—either straight-chained, e.g. allyl, 2-butenyl, 3-pentenyl, 1-hexenyl, 1-heptenyl, 1,3-hexadienyl or 1,3-octadienyl, or branched, e.g. isopropenyl, isobutenyl, isoprenyl, tert.-pentenyl, isohexenyl, isoheptenyl or isooctenyl.

Alkynyl—as a group per se and as structural element of other groups and compounds, such as alkynyloxy—is, in each case with due consideration of the specific number of carbon atoms in the group or compound in question and of the conjugated or isolated double bonds—either straight-chained, e.g. propargyl, 2-butinyl, 3-pentinyl, 1-hexinyl, 1-heptinyl, 3-hexen-1-inyl or 1,5-heptadien-3-inyl, or branched, e.g. 3-methylbut-1-inyl, 4-ethylpent-1-inyl, 4-methylhex-2-inyl or 2-methylhept-3-inyl.

Halogen-substituted groups, i.e. halogen-alkyl and halogen-alkoxy, may be partially halogenated or perhalogenated. Examples of halogen-alkyl—as a group per se and as a structural element of other groups and compounds, such as halogen-alkoxy—are methyl which is mono- to trisubstituted by fluorine, chlorine and/or bromine, such as $CHF_2$ or $CF_3$; ethyl which is mono- to penta-substituted by fluorine, chlorine and/or bromine, such as $CH_2CH_2F$, $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; and propyl or isopropyl which is mono- to hepta-substituted by fluorine, chlorine and/or bromine, such as $CH_2CHBrCH_2Br$, $CF_2CHFCF_3$, $CH_2CF_2CF_3$ or $CH(CF_3)_2$.

Preferred compounds are (1) Compounds of formula I, wherein
X and Y, independently of each other, are chlorine or fluorine, preferably fluorine; and
Z is hydrogen;

(2) Compounds of formula I, wherein
$R_1$ is $C_1$-$C_4$-alkyl, $C_1$-$C_4$-alkoxy or unsubstituted or one- or twofold substituted phenyl, the substituents being selected from the group consisting of $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, cyano-$C_1$-$C_2$-alkyl, cyano-$C_1$-$C_2$-haloalkyl, cyano-$C_1$-$C_2$-alkoxy, cyano-$C_1$-$C_2$-haloalkoxy, cyano-$C_1$-$C_2$-alkylthio or cyano-$C_1$-$C_2$-haloalkylthio, whereby when m or the number of substituents on phenyl independently from each other are more than 1, the substituents may be the same or different;
preferably $C_1$-$C_4$-alkyl, $C_1$-$C_4$-alkoxy or singly substituted phenyl, the substituents being selected from the group consisting of $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio or cyano-$C_1$-$C_2$-haloalkoxy, whereby when m is more than 1, the substituents may be the same or different;
more preferably $C_1$-$C_4$-alkyl, $C_1$-$C_2$-alkoxy or singly substituted phenyl, the substituents being selected from the group consisting of methyl, trifluoromethyl, trifluoromethoxy, trifluoromethylthio, cyanomethyl or cyanodifluoromethyl, whereby when m is more than 1, the substituents may be the same or different;
most preferably singly substituted phenyl, the substituents being selected from the group consisting of methyl, trifluoromethyl, trifluoromethoxy, trifluoromethylthio, cyanomethyl or cyanodifluoromethyl;

(3) Compounds of formula I, wherein
$R_2$ is $C_1$-$C_2$-alkyl, $C_1$-$C_2$-alkoxy, $C_2$-$C_4$-alkenyl, $C_2$-$C_4$-alkenyloxy, $C_3$-$C_8$-cycloalkyl or $C_3$-$C_8$-cycloalkyloxy;
preferably $C_1$-$C_2$-alkyl, $C_1$-$C_2$-alkoxy, $C_3$-$C_6$-cycloalkyl or $C_3$-$C_6$-cycloalkyloxy; more preferably $C_1$-$C_2$-alkyl or $C_1$-$C_2$-alkoxy;

(4) Compounds of formula I, wherein
$R_3$ is hydrogen;

(5) Compounds of formula I, wherein
$R_4$ is $C_1$-$C_4$-alkyl, $C_1$-$C_4$-haloalkyl, $C_3$-$C_8$-cycloalkyl, $C_3$-$C_8$-halocycloalkyl, $C_3$-$C_8$-cycloalkyl-$C_1$-$C_4$-alkyl or $C_3$-$C_8$-halocycloalkyl-$C_1$-$C_4$-alkyl;
preferably $C_1$-$C_2$-alkyl, $C_1$-$C_2$-haloalkyl, $C_3$-$C_6$-cycloalkyl or $C_3$-$C_6$-halocycloalkyl;
more preferably $C_1$-$C_2$-alkyl or $C_1$-$C_2$-haloalkyl;

(6) Compounds of formula I, wherein
m is 1 or 2;

(7) Compounds of formula I, wherein
X and Y, independently of each other, are chlorine or fluorine;
Z is hydrogen;
$R_1$ is $C_1$-$C_4$-alkyl, $C_1$-$C_4$-alkoxy or unsubstituted or one- or twofold substituted phenyl, the substituents being selected from the group consisting of $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, cyano-$C_1$-$C_2$-alkyl, cyano-$C_1$-$C_2$-haloalkyl, cyano-$C_1$-$C_2$-alkoxy, cyano-$C_1$-$C_2$-haloalkoxy, cyano-$C_1$-$C_2$-alkylthio or cyano-$C_1$-$C_2$-haloalkylthio, whereby when m or the number of substituents on phenyl independently from each other are more than 1, the substituents may be the same or different; and
m is 1 or 2;

(8) Compounds of formula I, wherein
X and Y are fluorine;
Z is hydrogen;
$R_1$ is $C_1$-$C_4$-alkyl, $C_1$-$C_4$-alkoxy or singly substituted phenyl, the substituents being selected from the group consisting of $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio or cyano-$C_1$-$C_2$-haloalkoxy, whereby when m is more than 1, the substituents may be the same or different; and
m is 1 or 2;

(9) Compounds of formula I, wherein
X and Y are fluorine;
Z is hydrogen;
$R_1$ is $C_1$-$C_4$-alkyl, $C_1$-$C_2$-alkoxy or singly substituted phenyl, the substituents being selected from the group consisting of methyl, trifluoromethyl, trifluoromethoxy, trifluoromethylthio, cyanomethyl or cyanodifluoromethyl, whereby when m is more than 1, the substituents may be the same or different; and
m is 1 or 2;

(10) Compounds of formula I, wherein
X and Y are fluorine;
Z is hydrogen;
$R_1$ is singly substituted phenyl, the substituents being selected from the group consisting of methyl, trifluoromethyl, trifluoromethoxy, trifluoromethylthio, cyanomethyl or cyanodifluoro-methyl; and
m is 1.

The following compounds of formula I are especially preferred:
2-(2,6-difluorophenyl)-4-(2-ethoxy-4-tert-butyl-phenyl)-4,5-dihydrooxazole (Etoxazole);
2-(2,6-difluorophenyl)-4-(4'-trifluoromethylbiphenyl-4-yl)-4,5-dihydrooxazole;
2-(2,6-difluorophenyl)-4-(4'-methylbiphenyl-4-yl)-4,5-dihydrooxazole;
2-(2,6-difluorophenyl)-4-(4'-trifluoromethoxybiphenyl-4-yl)-4,5-dihydrooxazole;
2-(2,6-difluorophenyl)-4-(4'-difluoromethoxybiphenyl-4-yl)-4,5-dihydrooxazole;
2-(2,6-difluorophenyl)-4-(4'-cyanodifluoromethoxybiphenyl-4-yl)-4,5-dihydrooxazole;

2-(2,6-difluorophenyl)-4-(4'-trifluoromethylthiobiphenyl-4-yl)-4,5-dihydrooxazole;
2-(2,6-difluorophenyl)-4-(4'-{1,1,2,2-tetrafluoroethoxy}-biphenyl-4-yl)-4,5-dihydrooxazole; and
2-(2-chloro-6-fluorophenyl)-4-(4'-trifluoromethoxybiphenyl-4-yl)-4,5-dihydrooxazole;

Particularly preferred are the following compounds:
2-(2,6-Dichlorophenyl)-4-(4'-trifluoromethylbiphenyl-4-yl)-4,5-dihydro-oxazole;
2-(2-Chloro-6-fluorophenyl)-4-(4'-trifluoromethylbiphenyl-4-yl)-4,5-dihydro-oxazole; and
2-(2,6-Difluorophenyl)-4-(4'-trifluoromethylbiphenyl-4-yl)-4,5-dihydro-oxazole.

Intensive fish farming sustains substantial economical losses through the injury of fish by parasites. Treatments against these parasites are known; the conventional active substances, however, must be used in relatively high concentrations and require long treatment periods. These active substances therefore cannot fully meet the requirements of a low-dose treatment, which is why there is still a need for the provision of further compounds having fish parasite-controlling properties, in particular for controlling fish-parasitic crustaceans, which object is achieved according to this invention by the use of compounds I.

In accordance with this invention the compounds of formula I are excellently suited for use in the control of fish parasites and, in particular, fish-parasitic crustaceans. These include the Copepodae (cyclops) with the genus *Ergasilus, Bromolochus, Chondracaushus, Caligus* (->*C. curtus, C. elongatus*), *Lepeophtheirus* (->*L. salmonis*), *Elythrophora, Dichelestinum, Lamproglenz, Hatschekia, Legosphilus, Symphodus, Ceudrolasus, Pseudocycmus, Lernaea, Lernaeocera, Pennella, Achthares, Basanistes, Salmincola, Brachiella, Epibrachiella, Pseudotracheliastes*;

and the families Ergasilidae, Bromolochidae, Chondracanthidae, Calijidae, Dichelestiidae, Philichthyidae, Pseudocycnidae, Lemaeidae, Lernaepotidae, Sphyriidae, Cecropidae, as well as the Branchiuriae (carp lice) with the families Argulidae and the genus *Argulus* spp.; and also the Cirripediae (barnacles) and *Ceratothoa gandichaugii*.

The fish include food fish, breeding fish and aquarium or pond fish of all ages occurring in freshwater, sea water and brackish water. The food fish and breeding fish include, for example, carp, eel, trout, whitefish, salmon, bream, roach, rudd, chub, sole, plaice, halibut, Japanese yellowtail (*Seriola quinqueradiata*), Japanese eel (*Anguilla japonica*), red sea bream (*Pagurus major*), sea bass (*Dicentrarchus labrax*), grey mullet (*Mugilus cephalus*), pompano, gilthread seabream (*Sparus auratus*), *Tilapia* spp., Cichlidae species such as plagioscion, channel catfish.

The compositions of this invention are particularly suitable for treating salmons. The term "salmon" within the scope of this invention will be understood as comprising all representatives of the family Salmonidae, especially of the subfamily salmonini and, preferably, the following species: Salmon *salar* (Atlantic salmon); Salmon *trutta* (brown or sea trout); Salmon *gairdneri* (rainbow trout); and the Pacific salmon (Oncorhynchus): *O. gorbuscha; O. keta; O. nekra; O. kisutch, O. tshawytscha and O. mason*; also comprised are artificially propagated species such as *Salvelinus* species and *Salmo clarkii*.

Preferred objects of the present invention are the Atlantic and Pacific salmon and the sea trout.

In present-day salmon and trout farming, juvenile fish are transferred in the smolt stage from fresh-water tanks to sea water cages. These latter are cubic, rectangular or also round cages having a metal frame which is covered with a fairly fine-meshed net. These cages are lowered into the sea until they are 9/10 submerged and then so anchored that they are accessible from the top.

In another variant, the fish are kept in sea water tanks of different shape. The cages are moored in sea inlets such that a constant flow of water passes through them in order to ensure a sufficient supply of oxygen. A constant flow of salt water in the sea water tanks is also maintained along with a supply of oxygen. In this artificial environment the fish are fed and, if necessary, provided with medication until they mature sufficiently for marketing as edible fish or are selected for further breeding.

Extremely intensive cage stocking is maintained in these fish farms. The fish density reaches orders of magnitude of 10 to 25 kg fish/$m^3$. In this pure monoculture, the exceedingly high fish densities coupled with the other stress factors cause the caged fish to become in general markedly more susceptible to disease, epidemics and parasites than their free-living co-specifics. In order to maintain healthy populations, the caged fish must be treated regularly with bactericides and permanently monitored.

Besides infectious diseases, the prime threat in commercial salmon farming is, however, attack by parasites, namely the representatives of the above-mentioned fish-parasitic crustaceans. In particular, two representatives of the class of Copepodae (cyclops) cause substantial losses in yield: *Lepeophtheirus* (*L. salmonis*) and *Caligus* (*C. elongatus*). These parasites are popularly known as sea lice. They are easily recognized: *Lepeophtheirus* has a brown, horseshoe-shaped carapace; *Caligus* is also brown, but much smaller.

These sea lice injure the fish by feeding on the scales, epithelium and the mucosa. When infestation is severe, these parasites also damage underlying dermis. If, moreover, infected salmon ar kept in cooler waters, then they are normally no longer able to protect themselves from these pests. As a consequence, secondary infections and water-logging will occur, even if the sea lice are removed. In extreme cases, severe wounding resulting from infest-ation by these parasites leads to further tissue damage caused by ultraviolet radiation or to the death of the fish from osmotic shock or the secondary infections.

Sea lice are meanwhile widely prevalent and encountered in all fish farms. Severe infestation kills the fish. Mortality rates of over 50%, based on sea lice infestation, have been reported from Norwegian fish farms. The extent of the damage depends on the time of year and on environmental factors, for example the salinity of the water and average water temperature. In a first phase, sea lice infestation is seen in the appearance of the parasites attached to the fish and later—even more clearly—from the damage caused to skin and tissue. The most severe damage is observed in smolts which are just in the phase in which they change from fresh water to sea water. The situation is made even worse by the specific conditions in the fish farms, where salmon of different age groups but of the same weight class are kept together; where fouled nets or cages are used; where high salt concentrations are to be found; where flow through the nets and cages is minimal and the fish are kept in a very narrow space.

Fish farmers who are confronted with this parasite problem usually suffer substantial financial losses and carry additional expenses. On the one hand, their fish are debilitated and damaged by the lice, resulting in lower rates of growth increase, and on the other hand, secondary infections have to be controlled with expensive drugs and labour-intensive measures. The fish can often no longer be sold, as the consumer will reject the damaged fish. This parasitic infestation can pose a threat to the salmon farmer's livelihood.

The worst damage is caused by *Lepeophtheirus*, as even few parasites cause widespread tissue damage. The life cycle of *Lepeophtheirus* consists substantially of two free-swimming larval stages (nauplius and copepodid stages), four chalimus stages, one pre-adult stage and the actual adult stage. The chalimus and adult stages are host-dependent.

The most dangerous stages, because they cause the greatest damage, are all those parasitizing on the fish, especially the actual adult stages.

Pest control agents which can be used to combat sea lice are commercially available, for example Trichlorfon (dimethyl-2,2,2-trichloro-1-hydroxyethylphosphonate), which requires concentrations of 300 ppm in sea water, and Dichlorvos (2,2-dichloroethenyldimethyl phosphate), which is effective from a concentration of 1 ppm. The shortcoming of these compounds is, however, the high concentrations in which they have to be used and the ecological problems associated therewith, which are of even greater consequence on account of the high half-life times.

Surprisingly, in the compounds of formula I, substances have been found which, while having very low toxicity to fish, is even more effective and, in particular, whose photolytic and hydrolytic degradability is more rapid as compared with the known sea lice control agents and, furthermore, which can be successfully used against all pre-adult and adult stages of sea lice on fish.

A further advantageous property of the compounds of formula I is that, at the proposed concentrations, other marine animals such as lobsters, oysters, crustaceans (with the exception of sea lice), fish and marine plants do not suffer injury. Its degradation products are in any case non-injurious to marine fauna and flora.

The fish are either treated orally, e.g. via their feed, or by bath treatment, for example in a "medicinal bath" wherein the fish are placed and where they are kept for a period of time (minutes to several hours) e.g. when being transferred from one breeding basin to another. In special cases treatment can also be carried out parenterally, for example by injection. It is also possible to treat the biotope of the fish temporarily or continuously, e.g. the net cages, entire ponds, aquaria, tanks or basins in which the fish are kept.

The active substance is administered in formulations which are adjusted to the applications. Formulations for oral administration are, for example, powders, granulates, solutions, emulsifiable concentrates or suspension concentrates which are mixed homogeneously as feed additives with the feed, or powders, granulates, solutions, emulsifiable concentrates or suspension concentrates which are administered in the form of pills, the outer coat of which can consist e.g. of fish feed compositions which cover the active substance completely. Formulations for bath application or for treating the biotope are powders, granulates, solutions, emulsions or suspensions, tablets or the active substance itself. The user may use these formulations in diluted or undiluted form.

The active substance in these formulations is used in pure form, as a solid active substance e.g. in a specific particle size or, preferably, together with—at least—one of the adjuvants which are conventionally used in formulation technology, such as extenders, typically solvents or solid carriers, or surface-active compounds (surfactants).

The formulations are prepared in a manner known per se, typically by mixing, granulating and/or compacting the active substance with solid or liquid carriers, where appropriate with the addition of further adjuvants, such as emulsifiable or dispersing agents, solubilisers, colourants, antioxidants and/or preservatives.

In practice it is also possible to use, for example, those forms of application where the active substance is contained in a readily water-soluble matrix of a film, or in films from which it diffuses over the period of application.

The active substance itself, in ground form or in one of the above formulations, can be used in water-soluble packagings, e.g. in polyvinyl alcohol bags which can be used together with the closed packaging. In this case the user in no longer exposed to the active substance or its formulation.

It is also possible to use semi-solid formulations for the bath treatment. The active sub-stance, which is suspended or dissolved in oily or fatty matrices, is washed out. The release can be controlled by the choice of adjuvants, concentration of the active substance and form (surface). Coprimates or melts of hard fats comprising the active substance are also suitable for use.

The diluted compositions of this invention are prepared by contacting the active substance of formula I with liquid and/or solid formulation assistants by stepwise mixing and/or grinding such that an optimal development of the antiparasitic activity of the formulation is achieved which conforms with the application.

The formulation steps can be supplemented by kneading, granulating (granulates) and, if desired, compressing (pills, tablets).

Formulation assistants can be, for example, solid carriers, solvents and, where appropriate, surface-active substances (surfactants) which are non-toxic for marine fauna and flora.

The following formulation assistants can be typically used for preparing the compositions of this invention:

Solid carriers are, for example, kaolin, talcum, bentonite, sodium chloride, calcium phos-phate, carbohydrates, cellulose powder, cotton seed meal, polyethylene glycol ether, if necessary binders such as gelatin, soluble cellulose derivatives, if desired with the addition of surface-active compounds such as ionic or nonionic dispersants; also natural mineral fillers such as calcite, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand.

In addition, a great number of pre-granulated materials of inorganic or organic nature can be used, e.g. especially dolomite or pulverized plant residues. The active substance can also be added to sorptive organic materials, such as polyacrylates, and be applied in this form.

Suitable solvents are: aromatic hydrocarbons which may be partially hydrogenated, preferably the fractions containing 8 to 12 carbon atoms, e.g. alkylbenzenes or xylene mixtures, alkylated napthalenes or tetrahydronaphthalenes, aliphatic or cycloaliphatic hydrocarbons such as paraffins or cyclohexane, alcohols such as ethanol, propanol or butanol, glycols and their ethers and esters, such as propylene glycol, dipropylene glycol ether, ethylene glycol or ethylene glycol monomethyl ether or ethylene glycol monoethyl ether, ketones such as cyclohexanone, isophorone or diacetanol alcohol, strongly polar solvents such as N-methyl-2-pyrrolidone, dimethyl sulfoxide or N,N-dimethyl formamide, water, as well as vegetable oils or epoxidized vegetable oils such as epoxidized rape-seed oil, castor oil, coconut oil or soybean oil, and silicone oils.

Depending of the type of formulation, suitable surface-active compounds are nonionic, cationic and/or anionic surfactants having good emulsifying, dispersing and wetting properties. The surfactants indicated hereinafter are only quoted as examples; the relevant literature describes many more surfactants which are conventionally used in formulation technology and which are suitable according to this invention.

Suitable nonionic surfactants are preferably polyglycol ether derivatives of aliphatic or cycloaliphatic alcohols, or saturated or unsaturated fatty acids, and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit. Illustrative examples of nonionic surfactants are nonylphenol polyethoxyethanols, polyethoxylated castor oil, polyadducts of polypropylene and polyethylene oxide, tributylphenoxy polyethoxyethanol, polyethylene glycol and octylphenoxy polyethoxyethanol. fatty acid esters of polyoxyethylene sorbitan are also suitable nonionic surfactants, typically polyoxyethylene sorbitan trioleate.

Cationic surfactants are preferably quaternary ammonium salts carrying, as substituent, at least one $C_8$-$C_{22}$alkyl radical and, as further substituents, optionally halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethyl ammonium bromide.

Suitable anionic surfactants may be water-soluble soaps as well as water-soluble synthetic surface-active compounds. Suitable soaps are the alkali metal salts, alkaline earth metal salts, ammonium salts or substituted ammonium salts of higher fatty acids ($C_{10}$-$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts. More often, however, so-called synthetic surfactants are used, especially fatty alcohol sulfonates, fatty alcohol sulfates, sulfonated benzimidazole derivatives or alkylarylsulfonates. The fatty alcohol sulfonates or sulfates are usually in the form of alkali metal salts, alkaline earth metal salts, ammonium salts or substituted ammonium salts, and they normally contain a $C_8$-$C_{22}$alkyl radical which also includes the alkyl moiety of acyl radicals, e.g. the sodium or calcium salt of ligninsulfonic acid, or dodecylsulfate, or of a mixture of fatty alcohol sulfates obtained from natural fatty acids. These compounds also comprise the salts of sulfated or sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphtha-lenesulfonic acid, or of a condensate of naphthalenesulfonic acid and formaldehyde. Corresponding phosphates, typically salts of the phosphoric acid ester of an adduct of p-nonylphenol with 4 to 14 mol of ethylene oxide, or phospholipids, are also suitable.

Suitable binders for water-soluble granulates or tablets are, for example, chemically modified polymeric natural substances which are soluble in water or in alcohol, such as starch, cellulose or protein derivatives (e.g. methyl cellulose, carboxymethyl cellulose, ethylhydroxy-ethyl cellulose, proteins such as gelatin and the like), as well as synthetic polymers, typically polyvinyl alcohol, polyvinyl pyrrolidone etc. Tablets may also contain, for example, fillers (e.g. starch, microcrystalline cellulose, sugar, lactose etc.), lubricants and disintegrators.

The bath application of the compositions of this invention to the parasites to be controlled can be carried out, for example, such that the compositions are placed in the cage in the form of solutions, emulsions, suspensions, powders or tablets, where they are quickly dissolved and dispersed by the movement of the fish and the flow of the water. Concentrated solutions can also be diluted with large volumes of water before being placed into the cages. Concentration problems do not normally occur in the cages because the fish, in expectation of food, move wildly whenever the cages are opened, thereby promoting fast dilution.

The antiparasitic compositions of this invention normally comprise 0.1 to 99%, preferably 0.1 to 95%, of active substance and 1 to 99.9%, preferably 5 to 99.9%,—at least—of a solid or liquid adjuvant, 0 to 25%, preferably 0.1 to 20%, of the composition preferably being surfactants (%=percent by weight). While concentrated compositions are sometimes preferred as commercial goods, the end user, e.g. for bath application, normally uses compositions which are diluted with water and which have a substantially lower active substance content. For example, in case of a bath treatment a concentration of from 0.005 to 2 ppm, preferably 0.01 to 1 ppm and in particular 0.05 to 0.5 ppm, active ingredient has turned out to be advantageously. Such compositions can contain further adjuvants, such as stabilizers, antifoams, viscosity regulators, binders, tackifiers as well as other active substances for achieving special effects. Preferred compositions are, in particular, composed as follows: (%=percent by weight):

| Emulsifiable concentrates: | |
| --- | --- |
| active substance: | 1 to 90%, preferably 5 to 20% |
| surfactant: | 1 to 30%, preferably 10 to 20% |
| solvent: | 5 to 98%, preferably 70 to 85% |
| Suspension concentrates: | |
| active substance: | 5 to 75%, preferably 10 to 50% |
| water: | 94 to 24%, preferably 88 to 30% |
| surfactant: | 1 to 40%, preferably 2 to 30% |
| Wettable powders: | |
| active substance: | 0.5 to 90%, preferably 1 to 80% |
| surfactant: | 0.5 to 20%, preferably 1 to 15% |
| solid carrier: | 5 to 99%, preferably 15 to 98% |
| Granulates: | |
| active substance: | 0.5 to 30%, preferably 3 to 15% |
| solid carrier: | 99.5 to 70%, preferably 97 to 85% |

The concentration of the active substance during application depends on the manner and duration of treatment and also on the age and condition of the fish so treated. In the case of short-term treatment, for example, it is from 0.1 to 10000 μg of active substance per liter of water, preferably from 0.5 to 10 μg per liter, at a treatment duration of e.g. 0.3-4 hours. In the case of pond applications it is possible to use e.g. from 0.01 to 50 μg of active substance per liter of water.

Formulations for application as feed additive are composed e.g. as follows:

| | | |
|---|---|---|
| a) | active substance: | 1 to 10% by weight |
| | soybean protein: | 49 to 90% by weight |
| | ground calcium powder: | 0 to 50% by weight |
| b) | active substance: | 0.5 to 10% by weight |
| | benzyl alcohol: | 0.08 to 1.4% by weight |
| | hydroxypropylmethyl cellulose: | 0 to 3.5% by weight |
| | water: | ad 100% by weight |

Preparation formulations for the bath application are, for example, the following emulsifiable concentrates, solutions, granulates or suspension concentrates:

FORMULATION EXAMPLES (%=percent by weight)

Example F1

Emulsifiable Concentrates

| | a) | b) | c) |
|---|---|---|---|
| active substance | 25% | 40% | 50% |
| calcium dodecylbenzene sulfonate | 5% | 8% | 6% |
| castor oil polyethylene glycol ether (36 mol EO) | 5% | — | — |
| tributylphenol polyethylene glycol ether (30 mol EO) | — | 12% | 4% |
| cyclohexanone | — | 15% | 20% |
| xylene mixture | 65% | 25% | 20% |

Emulsions of any required concentration can be produced from such concentrates by dilution with water.

Example F2

Solutions

| | a) | b) | c) | d) |
|---|---|---|---|---|
| active substance | 80% | 10% | 5% | 95% |
| ethylene glycol monomethyl ether | 20% | — | — | — |
| polyethylene glycol MG 400 | — | 70% | — | — |
| N-methyl-2-pyrrolidone | — | 20% | — | — |
| epoxidised coconut oil | — | — | 1% | 5% |
| benzine (boiling points 160-190° C.) | — | — | 94% | — |

These solutions are suitable for application in the form of microdrops.

Example F3

Granulates

| | a) | b) | c) | d) |
|---|---|---|---|---|
| active substance | 5% | 10% | 8% | 21% |
| kaolin | 94% | — | 79% | 54% |
| highly dispersed silicic acid | 1% | — | 13% | 7% |
| attapulgite | — | 90% | — | 18% |

The active substance is dissolved in dichloromethane, the solution is sprayed onto the carrier, and the solvent is subsequently removed by evaporation under vacuum.

Example F4

Emulsifiable Concentrate

| | |
|---|---|
| active substance | 10% |
| octylphenol polyethylene glycol ether (4-5 mol EO) | 3% |
| calcium dodecylbenzene sulfonate | 3% |
| castor oil polyglycol ether (36 mol EO) | 4% |
| cyclohexanone | 30% |
| xylene mixture | 50% |

Emulsions of any required concentration can be produced from such concentrates by dilution with water.

Example F5

Extruder Granulate

| | |
|---|---|
| active substance | 10% |
| sodium ligninsulfonate | 2% |
| carboxymethyl cellulose | 1% |
| kaolin | 87% |

The active substance is mixed with the adjuvants and the mixture is ground and moistened with water. This mixture is extruded, granulated and then dried in a stream of air.

Example F6

Coated Granulates

| | |
|---|---|
| active substance | 3% |
| polyethylene glycol (MG 200) | 3% |
| kaolin | 94% |

Example F7

Suspension Concentrate

| | |
|---|---:|
| active substance | 40% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active substance is homogeneously mixed with the adjuvants, giving a suspension concentrate from which suspensions of any desired concentration can be obtained by dilution with water.

The invention also concerns the use of chemical substances for the manufacture of compositions for injection into fish which are useful for the curative or preferably prophylactic treatment against fish parasites, especially sea lice. Particularly interesting is the use of antiparasitically active substances of the formula I in admixture with vaccine components, for the manufacture of a composition that gives active immunological protection against bacterial or viral diseases as well as conferring prophylactic protection against parasites, especially sea lice. Combining vaccine and prophylactic treatment in one product results in protection against bacterial, viral and/or parasitic diseases. The advantage of such a product is that it will neither cause additional stress to the fish nor additional workload for the fish farmer, because the use of injection vaccines against bacterial and viral diseases is already well established in the fish farming industry.

As injection preparations according to the invention, the compound of the formula I is normally not applied in pure form, but preferably in the form of a composition or preparation which contains, in addition to the active ingredient, application-enhancing constituents or formulation excipients, whereby such constituents are beneficial to the fish. In general, beneficial constituents are the formulation excipients for injection preparations which are physiologically tolerated by humans and animals and are known from pharmaceutical chemistry.

Such injection compositions or preparations to be used according to the invention usually contain 0.1 to 99% by weight, especially 0.1 to 95% by weight, of a substance that is active against sea lice, e.g. a compound of formula I, and 99.9 to 1% by weight, especially 99.9 to 5% by weight, of a liquid, physiologically acceptable excipient, including 0 to 25% by weight, especially 0.1 to 25% by weight, or a non-toxic surfactant and water.

Whereas it is preferred to formulate commercial products as concentrated injection formulations, the end user will also use dilute formulations.

The formulations suitable for injection are for example aqueous solutions of the active ingredients in water-soluble form, e.g. a water-soluble salt, in the broader sense also suspensions of the active ingredients, such as appropriate oily injectable suspensions, whereby e.g. to delay the release of active ingredient (slow release), suitable lipophilic solvents or vehicles are used, such as oils, e.g. sesame oil, or synthetic fatty acid esters, e.g. ethyl oleate, or triglycerides, or aqueous injectable suspensions containing viscosity-increasing agents, e.g. sodium carboxymethyl cellulose, sorbitol and/or dextran, and where appropriate stabilizers. Oil-containing formulations with delayed release of active ingredient are called depot preparations here and hereinafter, and they belong to the preferred embodiments of the present invention, since, especially in the case of prophylactic administration, they are able to protect the fish for long periods from an infestation by the sea lice.

Injectable compositions according to the invention can be formulated as a solution, suspension or emulsion of the antiparasitically active substance of the formula I, with or without vaccine components.

One preferred embodiment of the present invention is a composition for controlling fish parasites, characterized in that it is formulated as an injectable formulation containing as active principle either a compound of the formula I or a combination of a compound of the formula I together with vaccine component.

Examples of Injection Formulations

Example F8

Ampoule Containing the Active Ingredient, Disodium Pamidronat Pentahydrate and Water. After Dissolution (Concentration 3 Mg/Ml), the Solution can be Used for Injections

| | |
|---|---:|
| active ingredient | 15.0 mg |
| mannitol | 250 mg |
| water for injection | 5 ml |

Example F9

Injection Solution for Usage in an Inoculation Gun, Containing 25 g Active Ingredient in 10 Ampoules Each Containing 250 ml

| | |
|---|---:|
| active ingredient | 25.0 g |
| sodium chloride | 22.5 g |
| phosphate buffer solution (pH: 7.4) | 300.0 g |
| demineralized water | ad 2.500.0 ml |

Example F10

Injectables with Delayed Release of Active Ingredient

| Oily vehicles (slow release) | |
|---|---:|
| active ingredient | 0.1–1.0 g |
| groundnut oil | ad 100 ml |
| or | |

-continued

| Oily vehicles (slow release) | |
|---|---|
| active ingredient | 0.1-1.0 g |
| sesame oil | ad 100 ml |

The active ingredient is dissolved in part of the oil whilst stirring and, if required, with gentle heating, then after cooling made up to the desired volume and sterile-filtered through a suitable membrane filter with a pore size of 0.22 µm.

The active ingredient and the sodium chloride are dissolved in 1000 ml of demineralized water and the solution filtered through a micro-filter. The filtrate is mixed with the phosphate buffer solution and the resulting mixture diluted with demineralized water to a volume of 2500 ml and filled into 25 ml ampoules, each containing 1000 mg of active ingredient.

Example F11

Further Injection Formulations

11a: Aqueous Suspension

| active ingredient (micronized) | 1-5 g |
|---|---|
| povidone | 5 g |
| sodium chloride | 0.9 g |
| phosphate buffer solution | 10 g |
| benzyl alcohol | 2 g |
| water for injection | ad 100 ml |

11b: Solubilisate

| active ingredient | 0.1-0.5 g |
|---|---|
| POE-660-hydroxystearate | 15 g |
| propylene glycol | 65 g |
| benzyl alcohol | 4 g |
| water for injection | ad 100 ml |

11c: Oily Suspension

| active ingredient (micronized) | 1-5 g |
|---|---|
| medium-chained triglycerides (Miglyol 812) | ad 100 ml |

Table 1 presents a list of pure enantiomers of the compounds according to the invention, which are particularly well applicable in these formulations.

TABLE 1

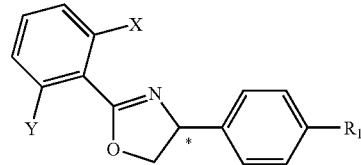

| No. | X | Y | $R_1$ | enantiomer | optical rotation[1] |
|---|---|---|---|---|---|
| 1.1 | F | F | $C_6H_4$-4-$CF_3$ | A | −24.3° (20.7 mg) |
| 1.2 | F | F | $C_6H_4$-4-$CF_3$ | B | +23.8° (21 mg) |
| 1.3 | F | F | $C_6H_4$-4-$CH_3$ | A | |

TABLE 1-continued

| No. | X | Y | $R_1$ | enantiomer | optical rotation[1] |
|---|---|---|---|---|---|
| 1.4 | F | F | $C_6H_4$-4-$CH_3$ | B | |
| 1.5 | F | F | $C_6H_4$-4-$OCF_3$ | A | |
| 1.6 | F | F | $C_6H_4$-4-$OCF_3$ | B | |
| 1.7 | F | F | $C_6H_4$-3-$CF_3$ | A | |
| 1.8 | F | F | $C_6H_4$-3-$CF_3$ | B | |
| 1.9 | F | F | $C_6H_4$-4-$OCF_2CHF_2$ | A | |
| 1.10 | F | F | $C_6H_4$-4-$OCF_2CHF_2$ | B | |
| 1.11 | F | F | $C_6H_4$-4-$OCHF_2$ | A | |
| 1.12 | F | F | $C_6H_4$-4-$OCHF_2$ | B | |
| 1.13 | F | F | $C_6H_4$-4-$SCF_3$ | A | |
| 1.14 | F | F | $C_6H_4$-4-$SCF_3$ | B | |
| 1.15 | F | F | $C_6H_4$-4-$CF_2CN$ | A | |
| 1.16 | F | F | $C_6H_4$-4-$CF_2CN$ | B | |
| 1.17 | F | F | $C_6H_3$-3-$CH_3$-4-$CF_3$ | A | |
| 1.18 | F | F | $C_6H_3$-3-$CH_3$-4-$CF_3$ | B | |
| 1.19 | F | Cl | $C_6H_4$-4-$OCF_3$ | A | |
| 1.20 | F | Cl | $C_6H_4$-4-$OCF_3$ | B | |

[1]$\alpha_D$ (589 nm $Na_D$), dissolved in 2 ml methanol

Biological Examples

1. Toxicity to Salmon Lice (In Vitro Test)

a) Collecting and Cultivating the Salmon Lice

Adult and pre-adult stages of the salmon louse are gently removed with broad forceps from naturally infected Atlantic salmon which have been kept in fish farms, separated according to stage and sex, and kept in sea water tanks at 10° C. and under continuous aeration. The sea water used for cultivating the lice comes from the fish farm from which the infected salmon have been taken. The tests themselves are carried out over 48 hours after collecting the lice.

b) In Vivo Test for Determining the Contact Action of the Control Agent

Into each of three test sets of three 500 ml-glass beakers, filled with sea water (salinity 33%, temperature 10° C.) containing 5, 500 and 5000 µg/l of the active substance, respectively, 5 female and 5 male adults of salmon lice are added. The beaker are then transferred to an incubator and held at 10° C. for 48 hours in the dark. Live survival of the salmon lice is determined at 1, 24 and 48 hours from the start of the exposure. All lice are examined and recorded as alive, moribund or dead.

The survival rate in this test after 24 hours is 0% throughout even in the lowest concentration of 5 µg/l for all three compounds, i.e. for 2-(2,6-Dichlorophenyl)-4-(4'-trifluoromethylbi-phenyl-4-yl)-4,5-dihydro-oxazole, 2-(2-Chloro-6-fluorophenyl)-4-(4'-trifluoromethylbiphenyl-4-yl)-4,5-dihydro-oxazole and 2-(2,6-Difluorophenyl)-4-(4'-trifluoromethylbiphenyl-4-yl)-4,5-dihydro-oxazole.

2. Toxicity Against Salmon Lice (In Vivo Test)

Five naturally infected Atlantic salmon are taken from the cage and transferred to well aerated sea water tanks. They remain there for 48 hours for acclimatization, and feed is withheld for 24 hours before the addition of test compound. A group of 5 salmon is treated at a concentration of 1.0 ppm of test compound, and a second group of 5 salmon is treated at a concentration of 0.1 ppm. The fish are kept for 24 hours in fresh sea water (without test compound) and a count is then made of dead and still living parasites. An untreated group of fish is also included in the evaluation. The test is carried out in triplicate.

Long lasting tests with 2-(2,6-Difluorophenyl)-4-(4'-trifluoromethylbiphenyl-4-yl)-4,5-dihydro-oxazole on salmon prove that 100% control is achieved even with one single treatment at 0.1 ppm for at least 3 month. Although the substance is very toxic for sea lice, it is well tolerated by fish.

What is claimed is:

1. A method of controlling fish parasites comprising treating a parasites selected from the group consisting of *Lepeophtheirus* and *Caligus* species with a composition comprising at least one compound of formula I wherein X and Y, independently of each other, are hydrogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, cyano-$C_1$-$C_4$-alkyl, cyano-$C_1$-$C_4$-haloalkyl, cyano-$C_1$-$C_4$-alkoxy, cyano-$C_1$-$C_4$-haloalkoxy, cyano-$C_1$-$C_4$-alkylthio, cyano-$C_1$-$C_4$-haloalkylthio, halogen, amino, cyano or nitro;

Z is hydrogen, halogen, $C_1$-$C_4$-alkyl, $C_1$-$C_4$-alkoxy or di($C_1$-$C_4$-alkyl)amino;

$R_1$ is $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen or unsubstituted or one- or twofold substituted phenyl, the substituents being selected from the group consisting of $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, cyano-$C_1$-$C_4$-alkyl, cyano-$C_1$-$C_4$-haloalkyl, cyano-$C_1$-$C_4$-alkoxy, cyano-$C_1$-$C_4$-haloalkoxy, cyano-$C_1$-$C_4$-alkylthio, cyano-$C_1$-$C_4$-haloalkylthio, $C_2$-$C_6$-alkenyl, $C_2$-$C_6$-haloalkenyl, $C_2$-$C_6$-alkenyloxy, $C_2$-$C_6$-haloalkenyloxy, $C_2$-$C_6$-alkinyl, $C_2$-$C_6$-haloalkinyl, $C_2$-$C_6$-alkinyloxy, $C_2$-$C_6$-haloalkinyloxy, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, OC(O)$R_2$ and halogen, wherein when m or the number of substituents on phenyl independently from each other are more than 1, the substituents may be the same or different;

$R_2$ is $C_1$-$C_4$-alkyl, $C_1$-$C_4$-alkoxy, $C_2$-$C_6$-alkenyl, $C_2$-$C_6$-alkenyloxy, $C_2$-$C_6$-alkinyl, $C_2$-$C_6$-alkinyloxy, $C_3$-$C_8$-cycloalkyl, $C_3$-$C_8$-cycloalkyloxy, $C_3$-$C_8$-halocycloalkyl-$C_1$-$C_4$-alkyl, $C_3$-$C_8$-halocycloalkyl-$C_1$-$C_4$-alkyloxy, N($R_3R_4$) or unsubstituted or mono- to pentasubstituted phenyl, wherein the substituents are selected from the group comprising $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano and nitro;

$R_3$ is hydrogen or $C_1$-$C_4$-alkyl;

$R_4$ is $C_1$-$C_4$-alkyl, $C_1$-$C_4$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, unsubstituted or mono to penta-substituted phenyl or unsubstituted or mono- to penta-substituted phenyl-$C_1$-$C_4$-alkyl, wherein independently of each other, the substituents are respectively selected from the group comprising $C_1$-$C_4$-alkyl; and m is 0, 1 or 2;

and their enantiomers, in each case either in free form or in the form of a salt;

and a carrier physiologically accepted by fish.

2. The method according to claim 1, wherein the composition is dissolved in ambient water containing the fish parasites.

3. The method according to claim 1, wherein the composition is added to feed provided to fish.

4. The method according to claim 1, wherein the composition is formulated into pills.

5. The method according to claim 1, wherein the fish parasites are at least one of *Lepeophtheirus salmonis* or *Caligus elongatus*.

6. The method according to claim 1, wherein X and Y are fluorine; and Z is hydrogen.

7. The method according to claim 1, wherein $R_1$ is $C_1$-$C_4$-alkyl, $C_1$-$C_2$-alkoxy or singly substituted phenyl, the substituents being selected from the group consisting of $C_1$-$C_2$-alkyl, $C_1$-$C_2$-halo alkyl, $C_1$-$C_2$-alkoxy, $C_1$-$C_2$-haloalkoxy, $C_1$-$C_2$-alkylthio, $C_1$-$C_2$-haloalkylthio and cyano-$C_1$-$C_2$-haloalkoxy, wherein when m is more than 1, the substituents may be the same or different.

8. The method according to claim 1, wherein $R_1$ is $C_1$-$C_4$-alkyl, $C_1$-$C_2$-alkoxy or singly substituted phenyl, the substituents being selected from the group consisting of methyl, trifluoromethyl, trifluoromethoxy, trifluoromethylthio, cyanomethyl and cyanodifluoromethyl, wherein when m is more than 1, the substituents may be the same or different.

9. The method according to claim 1, wherein $R_1$ is singly substituted phenyl, the substituents being selected from the group consisting of methyl, trifluoromethyl, trifluoromethoxy, trifluoromethylthio, cyanomethyl and cyanodifluoro-methyl.

10. The method according to claim 1, wherein $R_2$ is $C_1$-$C_2$-alkyl, $C_1$-$C_2$-alkoxy, $C_2$-$C_4$-alkenyl, $C_2$-$C_4$-alkenyloxy, $C_3$-$C_8$-cycloalkyl or $C_3$-$C_8$-cycloalkyloxy.

11. The method according to claim 1, wherein $R_2$ is $C_1$-$C_2$-alkyl or $C_1$-$C_2$-alkoxy.

12. The method according to claim 1, wherein m is 1 or 2.

13. The method according to claim 1, wherein X and Y, independently of each other, are chlorine or fluorine;

Z is hydrogen;

$R_1$ is $C_1$-$C_4$-alkyl, $C_1$-$C_4$-alkoxy or unsubstituted or one- or twofold substituted phenyl, the substituents being selected from the group consisting of $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio, cyano-$C_1$-$C_2$-alkyl, cyano-$C_1$-$C_2$-haloalkyl, cyano-$C_1$-$C_2$-alkoxy, cyano-$C_1$-$C_2$-haloalkoxy, cyano-$C_1$-$C_2$-alkylthio and cyano-$C_1$-$C_2$-haloalkylthio, wherein when m or the number of substituents on phenyl independently from each other are more than 1, the substituents may be the same or different; and m is 1 or 2.

14. The method according to claim 1, wherein X and Y are fluorine;

Z is hydrogen;

$R_1$ is $C_1$-$C_4$-alkyl, $C_1$-$C_4$-alkoxy or singly substituted phenyl, the substituents being selected from the group consisting of $C_1$-$C_2$-alkyl, $C_1$-$C_2$-haloalkyl, $C_1$-$C_2$-alkoxy, $C_1$-$C_2$-haloalkoxy, $C_1$-$C_2$-alkylthio, $C_1$-$C_2$-haloalkylthio and cyano-$C_1$-$C_2$-haloalkoxy, wherein when m is more than 1, the substituents may be the same or different; and m is 1 or 2.

15. The method according to claim 1, wherein X and Y are fluorine;

Z is hydrogen;

R$_1$ is singly substituted phenyl, the substituents being selected from the group consisting of methyl, trifluoromethyl, trifluoromethoxy, trifluoromethylthio, cyanomethyl and cyanodifluoro-methyl; and m is 1.

16. The method according to claim 1, wherein the compound of formula I is selected from the group consisting of:

2-(2,6-difluorophenyl)-4-(2-ethoxy-4-tert-butyl-phenyl)-4,5-dihydrooxazole;

2-(2,6-difluorophenyl)-4-(4'-trifluoromethylbiphenyl-4-yl)-4,5-dihydrooxazole;

2-(2,6-difluorophenyl)-4-(4'-methylbiphenyl-4-yl)-4,5-dihydrooxazole;

2-(2,6-difluorophenyl)-4-(4'-trifluoromethoxybiphenyl-4-yl)-4,5-dihydrooxazole;

2-(2,6-difluorophenyl)-4-(4'-difluoromethoxybiphenyl-4-yl)-4,5-dihydrooxazole;

2-(2,6-difluorophenyl)-4-(4'-cyanodifluoromethoxybiphenyl-4-yl)-4,5-dihydrooxazole;

2-(2,6-difluorophenyl)-4-(4'-trifluoromethylthiobiphenyl-4-yl)-4,5-dihydrooxazole;

2-(2,6-difluorophenyl)-4-(4'-{1,1,2,2-tetrafluoroethoxy}-biphenyl-4-yl)-4,5-dihydrooxazole; and 2-(2-chloro-6-fluorophenyl)-4-(4'-trifluoromethoxybiphenyl-4-yl)-4,5-dihydrooxazole.

17. The method of claim 1, wherein the fish are of the Salmonidae family.

18. The method according to claim 17, wherein the fish are selected from the group consisting of *Salmon salar, Salmon trutta, Salmon gairdneri, Oncorhynchus gorbuscha, Oncorhynchus keta, Oncorhynchus nekra, Oncorhynchus kisutch, Oncorhynchus tshawytscha, Oncorhynchus mamson, Salvelinus* species and *Salmo clarkii*.

19. The method according to claim 1, wherein the compound of formula I includes 2-(2,6-difluorophenyl)-4-(4'-trifluoromethylbiphenyl-4-yl)-4,5-dihydrooxazole.

* * * * *